(12) United States Patent
Koide (10) Patent No.: US 7,410,654 B2
(45) Date of Patent: Aug. 12, 2008

(54) POLLEN MANUFACTURING METHOD

(76) Inventor: Katsumi Koide, No. 30-7-108, Seizyo 9-chome, Setagaya-ku, Tokyo (JP)

( * ) Notice: Subject to any disclaimer, the term of this patent is extended or adjusted under 35 U.S.C. 154(b) by 521 days.

(21) Appl. No.: 11/045,096

(22) Filed: Jan. 31, 2005

(65) Prior Publication Data

US 2005/0170008 A1    Aug. 4, 2005

(30) Foreign Application Priority Data

Jan. 30, 2004    (JP)    ............................ 2004/22446

(51) Int. Cl.
*A61K 39/35*    (2006.01)
*A61K 35/64*    (2006.01)
*A61K 39/36*    (2006.01)
(52) U.S. Cl. .................... 424/539; 424/275.1
(58) Field of Classification Search ................ 424/539, 424/275.1; 530/379
See application file for complete search history.

(56) References Cited

U.S. PATENT DOCUMENTS

| 351,074 | A | * | 10/1886 | Robson | .................... | 5/110 |
| 2,669,066 | A | * | 2/1954 | Antles | .................... | 47/1.41 |
| 6,086,915 | A | * | 7/2000 | Zeligs et al. | ................ | 424/455 |

FOREIGN PATENT DOCUMENTS

| CN | 1391911 | * | 1/2003 |
| DE | 2922485 | A | * | 12/1980 |
| JP | 119/2001 | | 1/2001 |
| WO | WO2004004866 | * | 1/2004 |

OTHER PUBLICATIONS

Drews,RC, Annuels of Opthalmology, Jun. 1977, 9(6): pp. 781-784.*
Nath et. al, Cryobiology, Feb. 1975, 12.pp. 81-88.*

* cited by examiner

*Primary Examiner*—Courtney A Brown
(74) *Attorney, Agent, or Firm*—Jacobson Holman PLLC (57) ABSTRACT

Pollen is washed and cleaned, crushed and sterilized. Pollen particles are filtered through a filter device and the particles of less than 50 μm of diameter are taken out. Then the pollen particles are thrown into electrolysis reducing water including active hydrogen and having reduction ability, and particles are blended in the electrolysis reducing water obtaining a flowing water after an adjustment of the mixture liquid. The flowing water is forcibly sent to a super-fine-particle making apparatus in order to make the active oxygen disappear by means of active hydrogen in the electrolysis reducing water, which active oxygen is generated during the super-fine-particle making process. Accordingly, the whole pollen, including shells of pollen, super-fined without deterioration of the pollen ingredient and the pollen ingredient can be extracted from the super-fined pollen particles.

2 Claims, 7 Drawing Sheets

POLLEN MANUFACTURING METHOD

BACKGROUND OF THE INVENTION

1. Field of the Invention

The present invention relates to a pollen manufacturing method enabling to extract almost all pollen ingredient by means of crushing shells of the pollen gathered from bees or naturally adhered to flowers in order to make the all pollen including the shells super-fine one of nanometer size, without deterioration of the pollen ingredient.

2. Description of the Prior Art

Pollen is sexual cell of plant and adhesive so that when bees seek honey and they get honey from flowers, the adhesive pollen is adhered to the body hair of the bees. The bee gathers or collects pollen to his rear legs and makes the pollen round into a ball at a place called "press" between leg articulars of the rear legs. The pollen balls of a diameter of about 1 mm are stored in the part called "pollen basket" of his body, which basket is placed on the outside of the leg articulars, sunken at its center and surrounded with hair. It is said that the volume of pollen to be stored in the basket is about 20-30 mg. Bees bring the pollen and honey to the nest and store them in the nest. It is said that a mean volume of 145 g of pollen is necessary to grow up a male bee to an adult bee. It means that pollen includes nutritive substance ingredient necessary to live or survive and breed the bees.

However, the pollen has a grain or particle diameter of 10-100 μm and is protected by a hard double walled shell which is not broken by even using sulfuric acid, strong acid and strong alkali. As a result, it is not possible to us, human being to enjoy the benefit of the excellent nutritive substance except for breaking the shells of pollen.

According to the conventional pollen manufacturing method, enzyme treatment, fermentation treatment and mechanical treatment have been employed to break the shell of pollen. Japan Patent Application Publication No 119/2001 discloses a pollen manufacturing method for breaking pollen shell and taking pollen ingredient out of the pollen.

The enzyme treatment, fermentation treatment and breaking treatment according to the conventional pollen manufacturing method have merits and demerits and all of the conventional methods have problems of impossibilities of making pollen of super-fine-particles According to the prior art disclosed in Japan Patent Application Publication No 119/2001, a flowing material of pollen and some liquid is led to a super-fine-particle treatment apparatus under a high pressure, the shells of pollen are broken, the flowing material containing fine-particle pollen ingredient and the liquid is flown out, a liquid part of the flowing material is removed, and pollen ingredient is taken out.

The Japan Patent Application Publication No 119/2001 above fails to disclose clearly and sufficiently a pollen manufacturing method and a super-fine-particle manufacturing apparatus. The conventional pollen manufacturing method and super-fine-particle manufacturing apparatus disclosed in the Japan Patent Application Publication fails to firmly smash all pollen including the shells and surely break them, taking out the pollen ingredient.

The Japan Patent Application Publication No 119/2001 disclosed a method for removing liquid and the like from flowing material including pollen ingredient, in which method a spray-dry treatment for spraying hot air and evaporating the liquid is employed, so that effective or useful ingredient contained in the pollen, such as vitamins and the like, which are easy to be broken by thermal effect are disadvantageously destructed.

SUMMARY OF THE INVENTION

The present invention is invented to solve the problems above and provides a pollen manufacturing method for sending under a pressure a flowing material made of a mixture of pollen particles and an electrolysis reducing water obtained by electro-reducing tap water so as to have a reduction effect and active hydrogen characteristics to a super-fine-particle making apparatus, making pollen particles in the flowing material collide with each other under a high pressure, and breaking the shells of pollen in the apparatus.

The first object of the present invention is to prevent pollen ingredient from deteriorating due to its oxidization by making the active oxygen produced when the pollen particles in the flowing material collide with each other under a high pressure disappear by means of active hydrogen contained in the electrolysis reducing water.

The second object of the present invention is to provide a pollen manufacturing method making all of the pollen including super fine shells of nanometer size.

The third object of the present invention is to provide a pollen manufacturing method preventing the effective and useful ingredient such as vitamin and the like from being broken due to thermal effect and take out only pollen ingredient.

The objects above and other objects and novel characteristics of the present invention will be apparent from reading the following detailed explanation and the accompanying drawings, which are used to only explain the pollen manufacturing method according to the present invention and do not restrict the scope of the present invention.

DETAILED EXPLATION OF THE INVENTION

According to the present invention, the pollen taken out from bees and having about 1 mm of a diameter, and other pollen naturally stuck to flowers and sucked from the flowers are used as a raw material for the super-fine-particle manufacturing apparatus. Two kinds of the pollen above are differed in their diameters from each other and they are manufactured at different manufacturing steps. The pollen manufacturing method using the pollen taken from bees as a raw material is a first embodiment, and the pollen manufacturing method using the pollen naturally stuck to flowers and used as a raw material is a second embodiment of the pollen manufacturing method according to the present invention.

First Embodiment

The first step of the pollen manufacturing method according to the first embodiment of the present invention is a cleaning step for pollen taken from bees. That is, according to the first step of the pollen manufacturing method, the pollen of the raw material taken from bees has usually dirt adhered thereto and foreign matters such as dust contained in the pollen, so the pollen is immersed in water and circularly or repeatedly cleaned in order to remove dirt and foreign matters above completely.

The second step of the pollen manufacturing method is a crushing and sterilizing one for the pollen. Because that the pollen after the cleaning step has a large diameter of about 1 mm and they are rounded to a ball including miscellaneous bacterium taken while the pollen is being gathered by bees, the pollen balls are broken by means of water jet stream making fine particles, and the pollen fine particles are sterilized by means of a throwing step into, for example, a ultraviolet ray sterilization line.

The third step of the pollen manufacturing method of the present invention is a flowing material making step. That is, in the third step, the broken and sterilized pollen particles are filtered through a filter, obtaining the pollen particle of a diameter less than 50 μm, then 14-25 weight %, preferably 20 weight % of the filtered pollen particles is added to 75-85 weight %, preferably 80 weight % of an electrolysis reducing water obtained by electrolyzing tap water, which water showing an oxidized reducing electrical potential of minus value and active hydrogen characteristics, then they are blended and stirred in order to control the mixture liquid and make the pollen particles equally dispersed within the electrolyzed reducing water obtaining a flowing material of pollen particles and the electrolyzed reducing water.

The reason that electrolyzed reducing water, not tap water, is used is to prevent the pollen ingredient from being oxidized and from deteriorating due to chlorine included in tap water, as well from entering of foreign matters of tap water, and to utilize the active hydrogen characteristics of electrolyzed reducing water in the process of the pollen manufacturing method and to obtain high quality pollen ingredient.

It is not necessary to in particularly restrict the kind of electrolyzed reducing water. Preferably, the electrolyzed reducing water of electrolysis acid water and electrolyzed reducing water is used, which acid water and reducing water are produced by using, for example, an electrolyzed reducing water trimming apparatus of "Trim Ion TI-8000" made by Japan Trim Co, Ltd. It is known that the electrolyzed reducing water produced by the electrolyzed reducing water trimming apparatus has alkaline of about pH 9.6 and an oxidization reducing potential of about minus 274 mV, and includes active hydrogen.

"The electrolysis reducing water" above is obtained by using electrode plates made of titan plate platinum-baked in order to electrolyze tap water so that the electrolysis reducing water has rich or much active hydrogen provided with reducing forth and resultantly the power enable to neutralize various active oxygen. Ordinarily, two hydrogen atoms (H) are connected to each other becoming a hydrogen molecule ($H_2$), however, an active hydrogen has a hydrogen which does not exist as a molecule and exist in a shape of an atom.

While active oxygen is said to cause many diseases of human beings because strong oxidization power of the active oxygen breaks clean and pure cells of human beings, causing diseases of human beings and an acceleration of senility. Active oxygen is at an electrical unstable condition and has electrons fewer in number than that of an ordinal oxygen by one, causing to take (oxidize) electrons from a normal cell. As a result, the cell is oxidized and dried after its electrons are taken out by force.

Because the active hydrogen has a hydrogen of atom condition and electrically unstable, it is connected with active oxygen which are electrically unstable and causes many diseases of human beings, becoming harmful $H+O=H_2O$ water and drained out of a human body. It is said that active hydrogen has an elimination power for active oxygen.

The fourth step of the pollen manufacturing method of the present invention is an extraction one for breaking the shells of pollen and extracting an ingredient out of pollen. In detail, in the fourth step, whole pollen particles and shells containing the pollen particles in the flowing material of pollen particles and electrolysis reducing water are broken through the super-fine-particle making apparatus to, for example, a nanometer size, as well the ingredient in the pollen within the shells are extracted.

It is not necessary to restrict the super-fine-particle making apparatus to the particular one, and it is preferable to use, for example, the known "emulsification device" shown in FIG. 1 to FIG. 8 and of Japan Patent No 2788010 as a super-fine-particle making apparatus M structured with a flowing material storage tank 11, a high pressure pump 12 for the flowing material, a super-fine-particle making member 13 for making the flowing material forcibly flow by the high pressure pump 12 collide with each other under a high pressure to break the shells and making the whole pollen and shells of super-fine-particle of nanometer size in order to extract the pollen ingredient, and a store tank 14 for the flowing material including super-fine-particle pollen ingredient after the shells are broken and discharged from the super-fine-particle making member 13.

Concerning the super-fine-particle making member 13, the first disc 16 and the second disc 17 are adhered or connected firmly to each other and they are contained in the casing 15. These discs 16, 17 have through holes 16a, 16b and 17a, 17b, respectively having a width or diameter trough which the flowing material is able to flow and slit-like first and second guide grooves 16c, 17c. These through holes 16a, 16b and 17a, 17b and the guide grooves 16c, 17c form flow-in route 18, guide route 19, mixing chamber 20, and flow-out route 21, each of them will be explained in detail.

The first disc 16 and second disc 17 will be described with reference to FIGS. 2-6. These discs 16, 17 are made of wear resistance materials, such as sintered diamond and single crystal diamond and the like, of the same diameter.

Figure 1:
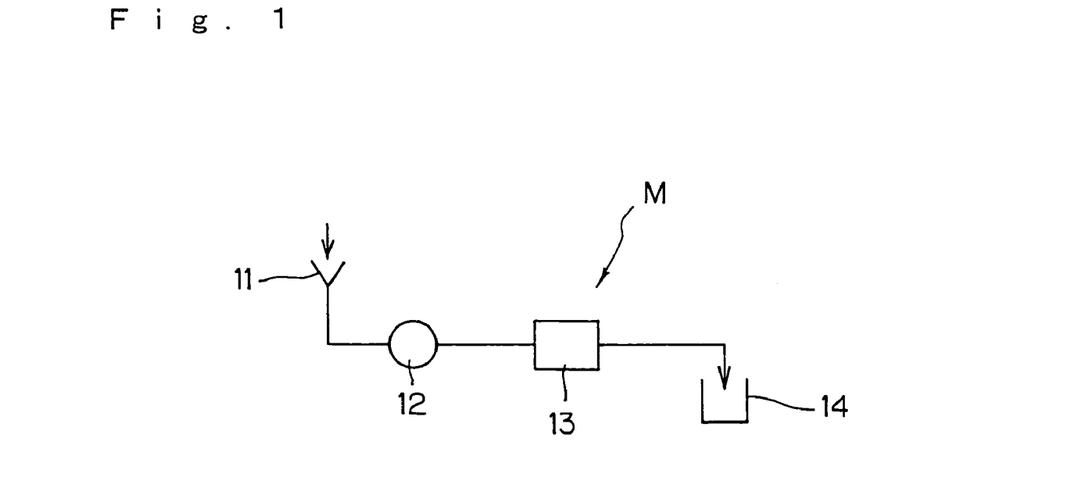
FIG. 1 is a diagram describing the whole system of the super-fine-particle making apparatus used for the pollen manufacturing method of the present invention.
Figure 2:
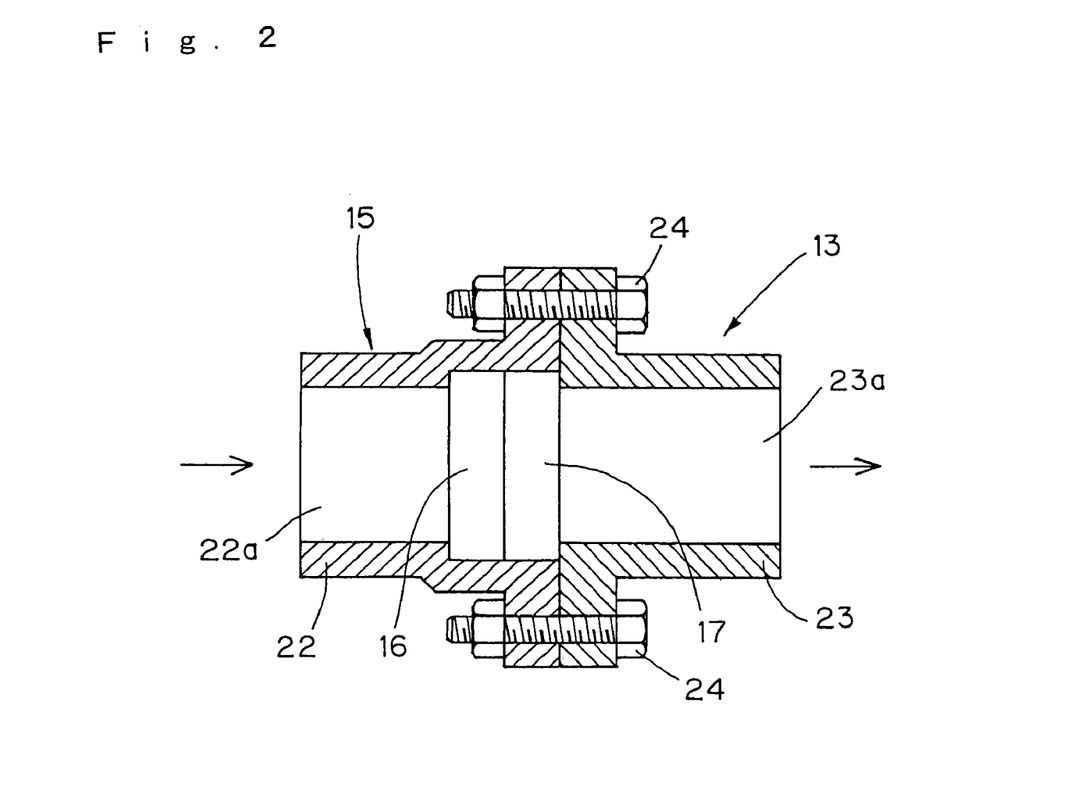
FIG. 2 is a schematic longitudinal sectional view of the super-fine-particle making apparatus used for the pollen manufacturing apparatus.
Figure 3:
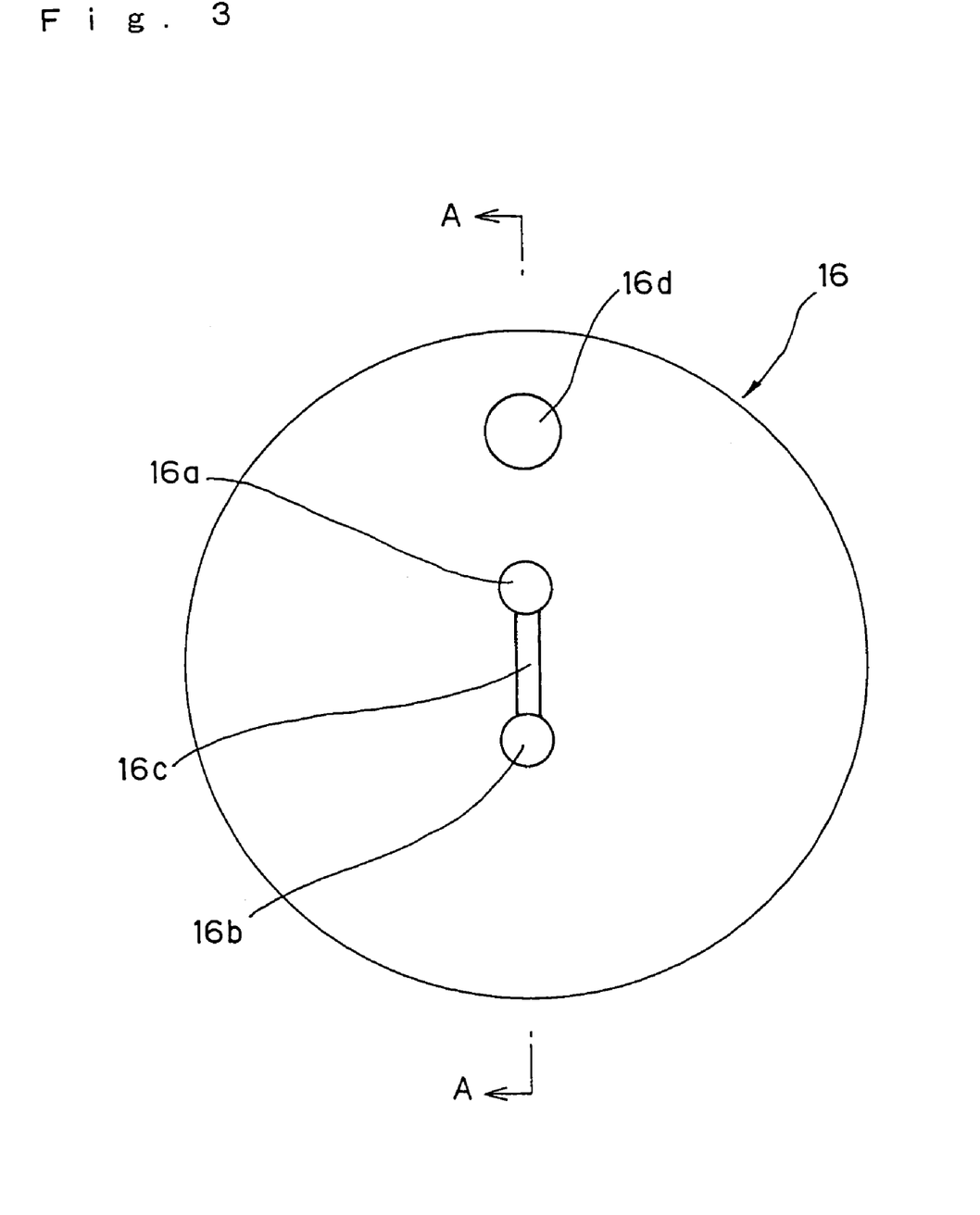
FIG. 3 is right side view of a first disc constructing the super-fine-particle making apparatus.
Figure 4:
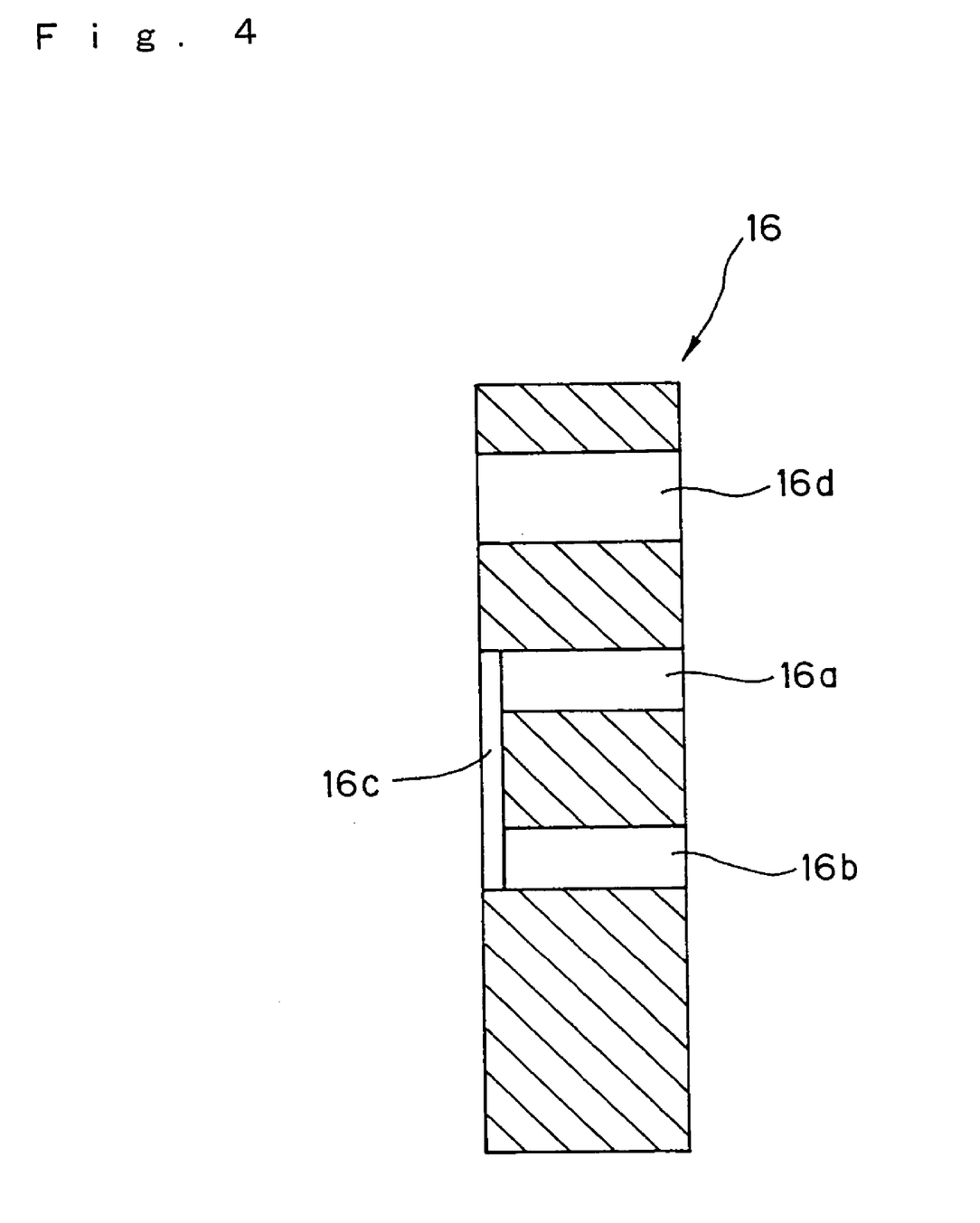
FIG. 4 is a longitudinal sectional view along line A-A of FIG. 3.
Figure 5:
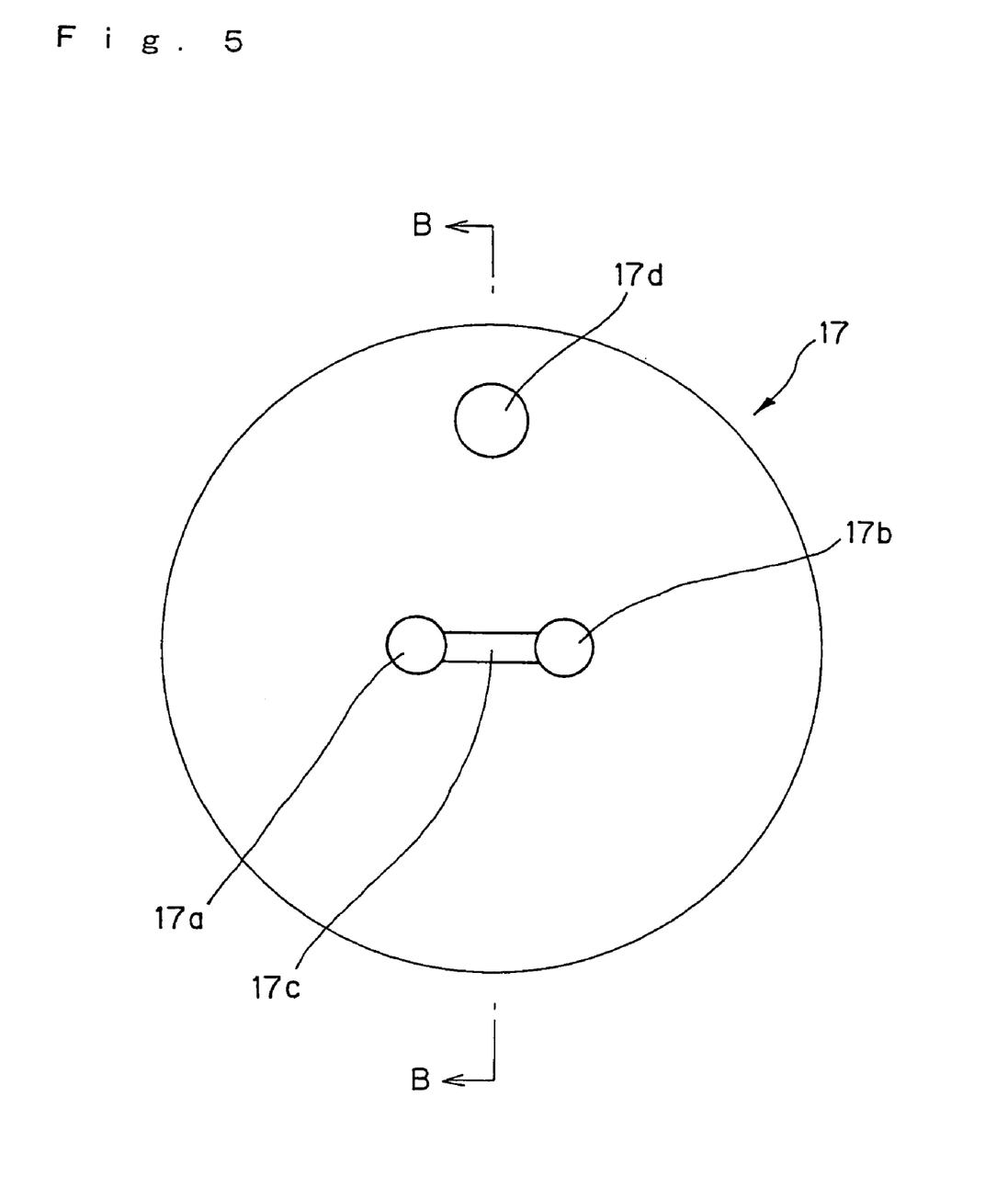
FIG. 5 is a left side view of a second disc constructing the super-fine-particle making apparatus used for the pollen manufacturing method of the present invention.
Figure 6:
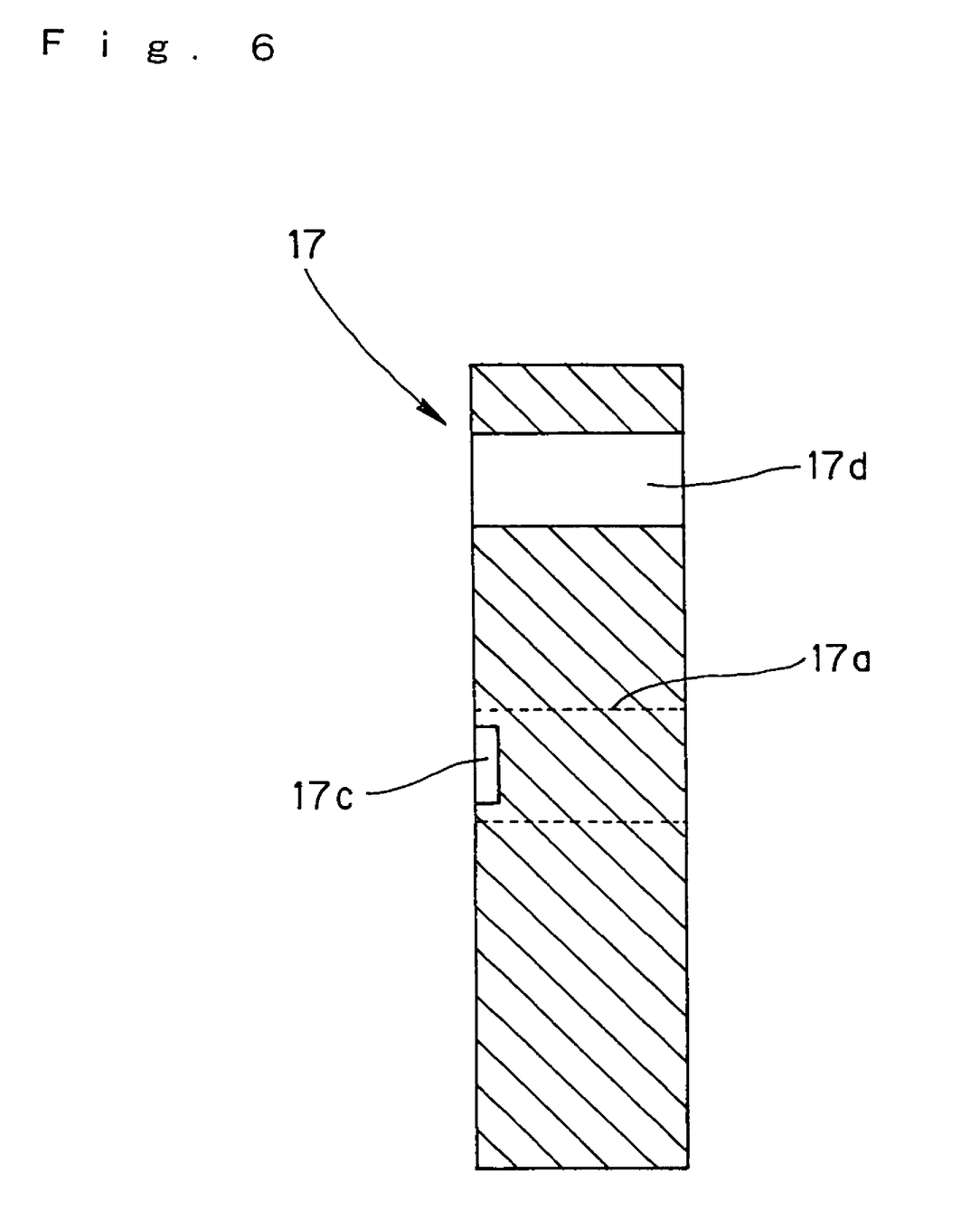
FIG. 6 is a longitudinal sectional view along line B-B of FIG. 5.
Figure 7:
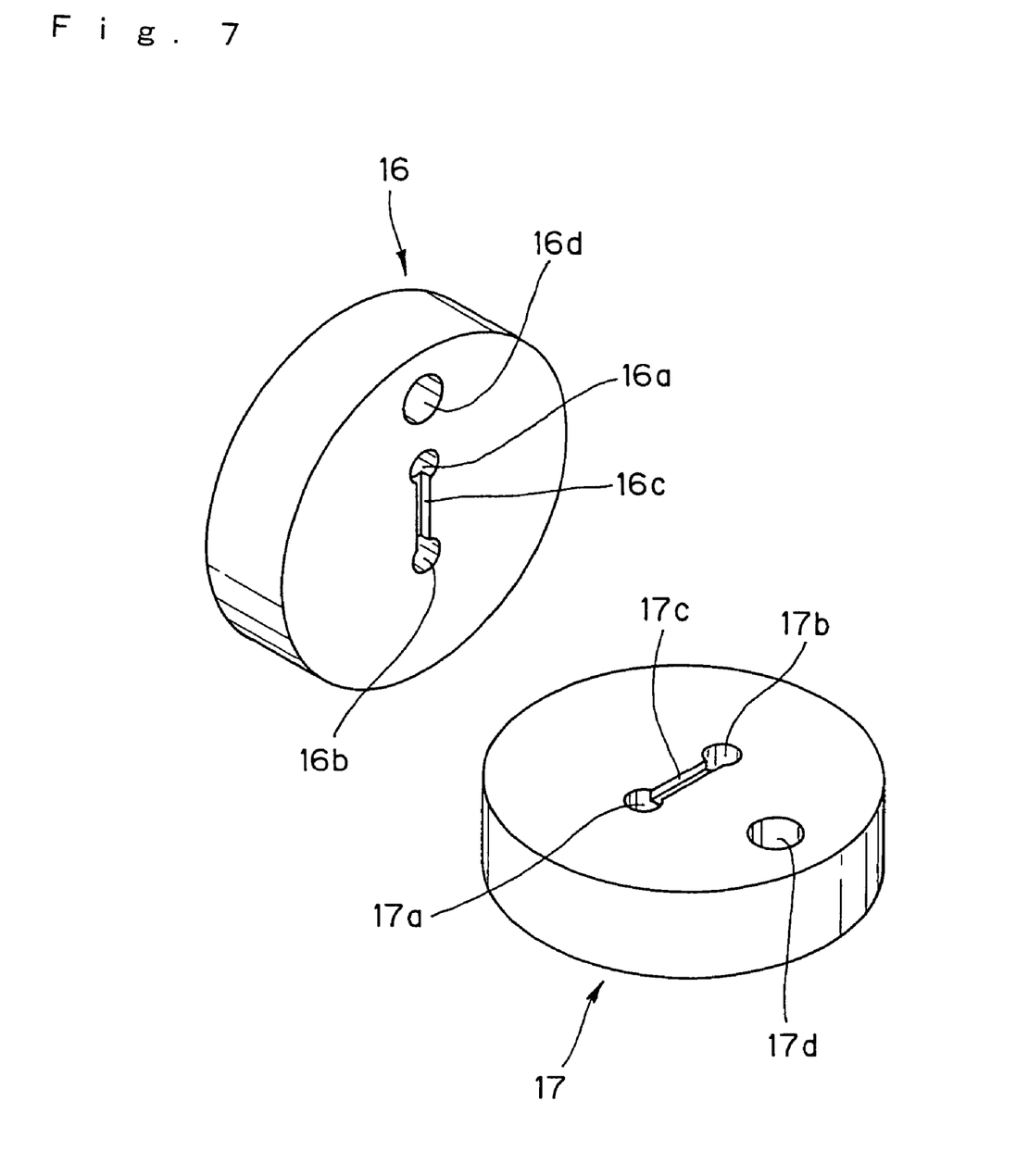
FIG. 7 shows a perspective view of the first disc and the second disc respectively constructing the super-fine-particle making apparatus used for the pollen manufacturing method of the present invention.

As shown in FIGS. 2, 3 and 6, these flow-in through holes 16a, 16b of the first disc 16 have the same diameter and are placed at the upper position and the lower position along a perpendicular line extending through a center of the first disc 16 at an identical distance from the center or at symmetrical positions. Furthermore, the first guide groove 16c of the first disc 16 is formed at the face of the disc 16 confronting and contacting with the second disc 17 so as to connect these through holes 16a, 16b.

As shown in FIGS. 3-7, the second guide groove 17c of the second disc 17 is formed at the face of the disc 17 confronting and contacting with the first disc 16 so as to connect these through holes 17a, 17b and to intersect at right angles with first guide groove 16c of the first disc 16.

These through holes 17a, 17b have the identical diameter and are place at both ends of the second guide groove 17c. The first and second discs 16 and 17, respectively provided with the structure mentioned above are placed one over another so as to make these straight first guide groove 16c and second guide groove 17c closely and firmly contact with each other and placed at an intersect line at right angles.

The first disc 16 and second disc 17 are placed within and contained in the casing 15, which is formed by connecting the first cylinder 22 and the second cylinder 23 with bolts 24, obtaining the super-fine-particle making member 13. An opening portion 22a formed on a side of the first cylinder 22 structuring the casing 15 is connected to the high pump 12, as well another opening portion 23a of the second cylinder 23 is connected to the store tank 14.

Figure 8:
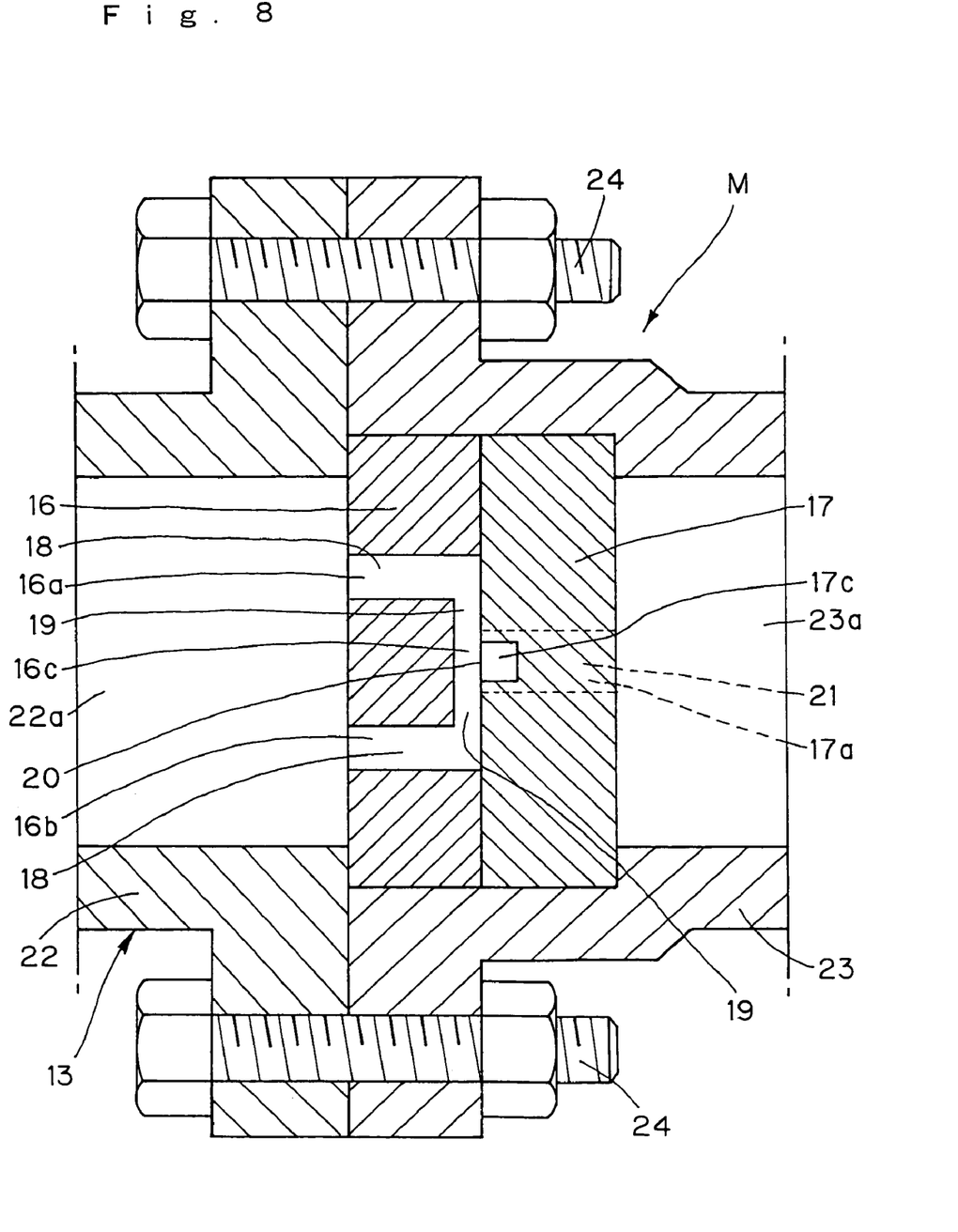
FIG. 8 is a longitudinal sectional view of an important portion of the super-fine-particle making apparatus used for the pollen manufacturing method of the present invention.

The first guide groove 16c and the second guide groove 17c, respectively of the first disc 16 and second disc 17 closely and firmly connected to each other in the casing 15, are crossed at right angles, forming a mixing chamber 20 at the centers of the first and the second discs 16, 17. Furthermore, the flow-in through holes 16a, 16b form the flowing route 18, the first guide groove 16c forms the guide route 19 directing to the center, and the flow-out through holes 17a, 17b and the second guide groove 17c form the flow-out route 21. Accordingly, as shown in FIG. 8, the flowing material flows through in order the flow-in route 18, guide route 19, mixing chamber 20 and flow-out route 21.

It is noted that the first and the second discs 16, 17 have the positioning through holes 16d, 17d for determining the right positions of these discs 16, 17. When these first and the second discs 16, 17 are intended to closely contact and fix to each other, the positioning through holes 16d, 17d must be placed to open to each other and to make pins (not shown) pass through the through holes 16d, 17de. As a result, the first and the second guide groves 16c, 17c are rightly crossed at right angles and the first and the second discs 16, 17 are rightly secured.

An operation of the super-fine-particle making apparatus M having the structure above will be explained. The flowing material stored in a supply tank 11 is forcibly sent to the opening portion 22a at one side of the casing 15 constructing the super-fine-particle making member 13 under about 130 Mpa by means of the high pressure pump 12.

The flowing material forcibly flown through the opening portion 22a flows in at a high speed through two flow-in through holes 16a, 16b of the first disc 16, and further through the flow-in route 18 formed by the flow-in through holes 16a, 16b and both end portions of the first guide groove 16c. Then, flowing material flows into guide routes 19, 19 which are formed with a face of said second disc 17 and said first guide groove 16c so as to make the flowing direction opposed to each other.

In the mixing chamber 20 formed at the centers of the discs and a crossing center of the first guide groove 16c and the second guide groove 17c, two opposed flowing materials of the flowing material severely collide with each other. Further, when the flowing material changes its flowing direction at a right angle along the second guide groove 17c crossed at a right angle to its flowing direction, substances of the flowing material collide to each other and making turbulent flows there and then collide to the wall of the second guide groove 17c making cavitations phenomena happen.

When these cavities or hollow portions of the phenomena are broken, high pressure difference is created at local positions and the solid (pollen) particles within the flowing material are broken. Such solid particles breaking phenomena happens instantaneously for a very short time of several micro second. As a result, very strong energy is applied instantaneously to the flowing material, whole pollen including shells become super-fine-particles owing to such huge energy, and all pollen content ingredient are effectively extracted.

When these pollen particles collide under a high pressure to each other and huge energy is added instantaneously to flowing material, water molecule dissolves and strong active oxygen such as OH radicals are created, resultantly such active oxygen reacts with pollen ingredient and the pollen ingredient is deteriorated. According to the pollen manufacturing method of the present invention, electrolysis reducing water containing active hydrogen is used and the active oxygen created in the super-fine-particle making process disappears, preventing the pollen ingredient from deteriorating.

Because that active hydrogen disappears within a very short time, it is necessary to add the electrolysis reducing water to the flowing material and mix them at every time of super-fine-particle making process if plural number of the making processes are carried out.

As described above, according to the pollen manufacturing method of the present invention, whole pollen and its shells are super-fine and all shells are broken. Resultantly, the flowing material are, after content ingredient of pollen is extracted, smoothly discharged to the flowing-out route 21, formed by a face of the first disc 16, and the second guide groove 17a and the flowing-out through holes 17a, 17b being stored in the storing tank 14. During the flowing material passing through the flowing-out route 21, it collides with the wall opposing to the mixing chamber 20 and end walls connected to the flow-out through holes 17a, 17b, resultantly a fine-particle making process is furthermore developed or proceeds.

That is, two discs 16, 17 of the super-fine-particle manufacturing apparatus M are overlapped and closely secured, so that the flowing material passes through the slit-like guide grooves 16c, 17c formed on the overlapped faces of the discs 16, 17, changes its flowing direction so as to collide with these walls and with mutually the materials in the flowing material. So that pollen and shells are surely super-fined obtaining super-fined particles. The super-fined particles are discharged out of the casing 15 and stored in the store tank 14. The flowing material is treated until the particle size of pollen charged into the super-fine-particle making apparatus M becomes, for example, of several nanometer in diameter. That is, the flowing material stored in the storing tank 14 is forcibly sent to the opening portion 12a by means of the high-pressure pump 12 and to several super-fine-particle making apparatus M. The super-fine-particle making process is repeated, so it is possible to obtain the pollen particulars fine to the predetermined diameter ones.

It is noted that at each time of charging the flowing material into the super-fine-particle making apparatus M, 5-50 weight %, preferably 10 weight % of electrolysis reducing water is newly added to the flowing material and mixed to each other in order to make the active oxygen repeatedly generated in the new super-fine-particle making process disappear by means of active hydrogen of the new electrolysis reducing water.

In case that the electrolysis reducing water is of alkaline of about 9-10 pH, an extraction efficiency of pollen ingredient from super-fine pollen particles increases and almost all pollen ingredient contained in the pollen particles is able to be extracted in the flowing material.

The fifth step of the pollen manufacturing method according to the present invention is a drying one. In detail, in the fifth step, the flowing material containing super-fine-particles of pollen and content ingredient extracted from the pollen in the fourth step is freeze-dried in order to evaporate water content in the flowing material and take out the super-fine-particles of pollen ingredient in a shape of dried ball-like pollen ingredient.

According to the pollen manufacturing method of the present invention, a freeze-dry technique is used, not a heat dry one using a spray dryer. The freeze-dry technique freezes the flowing material to a temperature of about minus 40° C. and then it is restored to an ordinal temperature gradually for about 12 hours in order to evaporate water content in the flowing material and take out pollen ingredient. Because that such freeze-dry technique is applied to the pollen manufacturing method of the present invention, it is possible to prevent effective ingredient of pollen such as vitamin and the like from being broken due to heat.

On the contrary, the conventional heat-dry technique using a spray dryer for frying the flowing material with a heat of about 180° breaks the ingredient which is sensitive to thermal effect such as vitamin and the like, so it is not possible to employ the conventional technique in the pollen manufacturing method of the present invention.

The sixth step of the pollen manufacturing method of the present invention is a crushing one for dried pollen ingredient.

In detail, the ball-like dried pollen ingredient formed in the fifth step of drying and evaporating water content of the pollen is finely crushed to obtain the last product of powder like dried pollen ingredient or coined tablet like solid pollen ingredient by means of a crusher of the predetermined diameter of pollen ingredient.

After the sixth step of the pollen manufacturing method is completed, the powder products are wrapped as they are and the solid products are coined, and they are shipped as commodities.

Second Embodiment

The second embodiment of the pollen manufacturing method of the present invention uses the pollen, which is naturally adhered to flowers and sucked from the flowers as a raw material. The pollen adhered to flowers and sucked from the flowers have different diameters from that of the pollen collected from bees and the diameter of the bee's pollen is about 20-100 µm. Accordingly, only the first, second and third steps of the pollen manufacturing method according to the second embodiment of the present invention are a little differed from that of the pollen manufacturing method according to the first embodiment using pollen collected from bees and these steps after the third step are identical with that of the first embodiment.

The pollen manufacturing method according to the second embodiment will be explained in detail.

The first step of the pollen manufacturing method of the second embodiment of the present invention using the pollen adhered to flowers and sucked from the flowers is a cleaning step for cleaning the pollen taken out of flowers. In detail, because the raw material of the pollen taken out of flowers has dirt adhered thereto and dust and other foreign matter from the pollen.

The second step of the second embodiment of the pollen manufacturing method according to the present invention, which embodiment uses the pollen naturally adhered to flowers and sucked out of the flowers, is a pollen sterilization one. In detail, because the pollen, even after the cleaning step applied to the pollen, has miscellaneous bacteria attached thereto during a sucking and taking out process of pollen, the pollen is placed on, for example, an ultraviolet rays sterilization line and is sterilized thereon.

In the third step of the pollen manufacturing method according to the second embodiment using the pollen naturally adhered to flowers and taken out by sucking is a mixed liquid adjustment one. In detail, according to the third step of the pollen manufacturing method, the pollen sterilized is filtered through a filter in order to take out the fine pollen particles of a diameter less than 50 µm, then the pollen particles are added to and mixed with 75-85 weight %, preferably 80 weight % of electrolysis reducing water, which is produced by means of carry-out of an electrolysis operation on tap water so as to have about pH 9-10 of alkaline, a low oxygen reducing potential, and include active hydrogen, and finally the mixture liquid is controlled so as to evenly scatter and mix the pollen particles in the electrolysis reducing water and obtain a flowing material of pollen particles and electrolysis reducing water. The reason that electrolysis reducing water, not tap water, is used is to prevent pollen ingredient from being oxidized owing to chlorine included in tap water, from being deteriorated, and from being invaded of non-pure materials. Furthermore, in order to obtain high grade pollen ingredient, the characteristics of electrolysis reducing water is employed in the pollen manufacturing method of the present invention.

These fourth-sixth steps of the pollen manufacturing method are identical with these of the pollen manufacturing method using bee pollen in the first embodiment, so that a detailed explanation for these steps are omitted.

According to the pollen manufacturing method of the present invention, the flowing material including pollen particles and electrolysis reducing water provided by electrolyzing tap water so as to have reduction feature and include active hydrogen is thrown into the super-fine-particle making apparatus, after the pollen particles and electrolysis reducing water are blended, in which apparatus pollen particles collide with each other under a high pressure so as to crush the shells without deterioration of the pollen ingredient, and make them of super-fine, extracting the content ingredient of the pollen in the flowing material. So that, the pollen ingredient is taken out at a condition of the flowing material, the flowing material can be freeze-dried to remove water content wherefrom, and only pollen ingredient can be taken out without breaking vitamin and the like due to thermal effect effective thereto.

It is apparent that the pollen manufacturing method of the present invention has an excellent effect, improving human health, because the pollen ingredient is made in a shape of powder or tablets, and it is possible to easily eat the pollen ingredient as a health supplement.

In accordance with the experiments of super-fine pollen ingredient obtained by the first and second embodiments of the pollen manufacturing method of the present invention, the pollen ingredient was given to 100 patients of hospitals in Tokyo district for about one month at a rate of 3 g per person a day. Very much good effect of the pollen ingredient was seen on the patients of pollen disease, asthma, atopic dermatitis, allergic dermatitis, the prostatitis, prostate obesity, whole body fatigue, and wearness.

What is claimed is:

1. A pollen manufacturing method comprising:
a first step of cleaning pollen taken from bees to remove dirt and foreign matters on the pollen,
a second step of crushing the cleaned pollen obtaining fine-pollen-particles and sterilizing the crushed pollen particles,
a third step of filtering the crushed and sterilized pollen particles by a filter so as to take out the pollen particles of a diameter less than 50 µm, and then entering the pollen particles of 15-25 weight % into electrolysis reducing water of 75-85 weight % produced by electrolyzing tap water so as to have a reduction property and active hydrogen, stirring and adjusting the mixture so as to evenly scatter the pollen particles in the electrolysis reducing water, obtaining a flowing material of the pollen particles and electrolysis reducing water, a fourth step of charging the flowing water and pollen particles scattered therein to a super-fine-particle making apparatus having two discs with through holes and the two discs being interconnected by guide grooves arranged perpendicular to each other, respectively, to form a mixing chamber there between of turbulent fluid flow and cavitation, making the pollen particles of the flowing material collide with each other under a high pressure, crushing the shells, and entering the electrolysis reducing water of about 9-10 pH at 5-20 weight % into the flowing material, mixing, and an adding-mixing operation being carried out several times repeatedly in order to make whole pollen fine at every charge, a fifth step of freeze-drying the flowing material having the super-fine pollen particles, evaporating water in the flowing material, and taking out the super-fine pollen particles in a shape of a dried ball-like pollen ingredient, and a sixth step of crushing the dried ball-like pollen ingredient to a predetermined diameter.

2. A pollen manufacturing method comprising a first step of cleaning pollen taken from flowers in order to remove dirt and foreign matter in the pollen, a second step of sterilizing the cleaned pollen, a third step of filtering the sterilized pollen by a filter to take out pollen particles of a diameter less than 50 μm, then entering the pollen particles of 15-25 weight % into electrolysis reducing water of 75-85 weight % produced by electrolyzing tap water so as to have a reduction property and active hydrogen, stirring and adjusting the mixture so as to evenly scatter pollen particles in the electrolysis reducing water, and obtaining a flowing material of pollen particles and electrolysis reducing water, a fourth step of charging the flowing material of electrolysis reducing water and pollen particles scattered therein to a super-fine-particle making apparatus having two disc with through holes and the two discs being interconnected by guide grooves arranged perpendicular to each other, respectively, to form a mixing chamber there between of turbulent fluid flow and cavitation, making the pollen particles of the flowing material collide with each other under a high pressure, crushing the shells, and entering the electrolysis reducing water of about 9-10 p at 5-20 weight % into the flowing material, mixing, and an adding-mixing operation being carried out several times repeatedly, in order to make whole pollen fined at every time of charging, a fifth step of freeze-drying the flowing material having the super-fined pollen particles, evaporating water content of the flowing material, and taking out the super-fined pollen particles in a shape of a dried ball-like pollen ingredient, and a sixth step of crushing the dried ball-like pollen ingredient to a predetermined diameter.

* * * * *